(12) United States Patent
Hayes et al.

(10) Patent No.: US 6,334,980 B1
(45) Date of Patent: Jan. 1, 2002

(54) FLEXIBLE APPARATUS WITH ABLATION FORMED CHAMBER(S) FOR CONDUCTING BIO-CHEMICAL ANALYSES

(75) Inventors: Donald J. Hayes, Plano; David B. Wallace, Dallas; Christopher J. Frederickson, Little Elm, all of TX (US)

(73) Assignee: Microfab Technologies Inc., Plano, TX (US)

( * ) Notice: Subject to any disclaimer, the term of this patent is extended or adjusted under 35 U.S.C. 154(b) by 0 days.

(21) Appl. No.: 09/163,063

(22) Filed: Sep. 25, 1998

Related U.S. Application Data

(62) Division of application No. 08/524,477, filed on Sep. 7, 1995, now Pat. No. 5,849,208.

(51) Int. Cl.[7] .......................... G01N 15/00; G01N 1/00; C12P 19/34; C12Q 1/68; C12M 1/00
(52) U.S. Cl. ................. 422/68.1; 422/50; 422/129; 422/131; 422/134; 422/138; 435/4; 435/6; 435/91.2; 435/283.1; 435/285.1; 435/285.2; 435/286.1; 435/286.5; 435/287.1; 435/287.2; 435/287.3; 435/287.9; 435/289.1; 435/297.1; 435/303.1
(58) Field of Search ................. 435/6, 5, 4, 91.2, 435/283.1, 285.1, 285.2, 286.1, 286.5, 287.1, 287.2, 287.3, 287.9, 289.1, 297.1, 303.142; 422/50, 68.1, 129, 131, 134, 138

(56) References Cited

U.S. PATENT DOCUMENTS

| | | | |
|---|---|---|---|
| 5,035,862 A | | 7/1991 | Dietze et al. |
| 5,133,937 A | | 7/1992 | Frackleton et al. |
| 5,182,427 A | * | 1/1993 | McGaffigan et al. ..... 219/10.75 |
| 5,188,963 A | | 2/1993 | Stapleton |
| 5,229,297 A | * | 7/1993 | Schnipelsky et al. ......... 436/94 |
| 5,333,675 A | | 8/1994 | Mullis et al. |
| 5,405,510 A | | 4/1995 | Betts et al. |
| 5,474,796 A | | 12/1995 | Brennan |
| 5,500,071 A | | 3/1996 | Kaltenbach et al. |
| 5,589,136 A | | 12/1996 | Northrup et al. |
| 5,593,130 A | * | 1/1997 | Hansson et al. ........... 251/61.1 |
| 5,632,957 A | * | 5/1997 | Heller et al. ................ 422/68.1 |
| 5,639,423 A | * | 6/1997 | Northrup et al. ............. 122/50 |
| 5,653,939 A | * | 8/1997 | Hollis et al. .................. 422/50 |
| 5,736,188 A | * | 4/1998 | Alcock et al. ............. 427/2.11 |
| 5,859,074 A | * | 1/1999 | Rezai et al. .................. 521/54 |
| 5,932,485 A | * | 8/1999 | Schofield et al. ........... 438/690 |
| 6,152,920 A | * | 11/2000 | Thompson et al. ........... 606/41 |

OTHER PUBLICATIONS

Christian C. Oste, ""PCR Instrumentation: Where Do We Stand?"," Teh Polymerase Chain Reaction, Birkhause, Boston, p. 165–173, (Jan. 15, 1994).

(List continued on next page.)

Primary Examiner—Ardin H. Marschel
(74) Attorney, Agent, or Firm—Locke Liddell & Sapp LLP

(57) ABSTRACT

Miniaturized, self-contained apparatus for conducting biochemical reactions and analyses is formed in a compact structure comprising a substrate which includes a plurality of reaction chambers and a plurality of analysis chambers which are in fluid communication with the reaction chambers. Independently controllable heaters and coolers are positioned in thermal contact with the reaction chambers to permit parallel processing of biological samples at different temperature cycles. The apparatus is especially useful for performing and analyzing the results of a polymerase chain reaction.

53 Claims, 11 Drawing Sheets

OTHER PUBLICATIONS

Eggers, Hogan, Reich, Lamture, Ehrlich, Hollis, Kosicki, Powdrill, Beattie, Smith, Varma, Gangadharam, Mallik, Burke and Wallace, ""A Microchip for Quantitative Detection of Molecules Utilizing Luminescent and Radioisotope Reporter Groups"," BioTechniques, vol. 17 (No. 3), pp. 516–523, (Jan. 15, 1994).

Fodor, Rava, Huan, Pease, Holmes and Adams, ""Multiplexed Biochemical Assays with Biological Chips"," Nature, p. 555, (Aug. 5, 1993).

Harrison, Fluri, Seiler, Fan, Effenhauser, Manz, ""Micromachining a Miniaturized Capillary Electrophoresis–Based Checmical Analysis System on a Chip"," Science, p. 895, (Aug. 13, 1993).

Bloomstein and Ehrlich, ""Laser–Chemical Three–dimensional Writing for Microelectromechanics and Application to Standard–cell Microfluidics"," J. Vac. Sci. Technol. B, p. 2671, (Nov. 15, 1992).

* cited by examiner

FLEXIBLE APPARATUS WITH ABLATION FORMED CHAMBER(S) FOR CONDUCTING BIO-CHEMICAL ANALYSES

CROSS REFERENCE TO RELATED APPLICATION

This application is a division of parent patent application No. 08/524,477, now U.S. Pat. No. 5,849,208 filed Sep. 7, 1995 by the same inventors for which benefit is claimed under 35 U.S.C. §120.

This invention relates to bio-chemical analysis. More particularly, it relates to miniaturized unitary analysis apparatus in which a reaction chamber, a heater and an analysis chamber are formed to permit rapid thermo-cycling and analysis of bio-chemical reactions.

Genetic testing of DNA and related materials is an integral part of clinical, commercial and experimental biology. In the medical field, for example, genetic tests are critical for effective treatment of cancer and inherited diseases. Oncologists use genetic tests to obtain the cytogenetic signature of a malignancy which in turn guides the choice of therapy and improves the accuracy of prognoses. Similarly, monitoring frequency and type of mutations persisting after chemotherapy or radiation therapy provides quick and accurate assessment of the impact of the therapy. Perhaps the most important application of molecular diagnosis in oncology is the emerging possibility of using antisense genetic therapy to combat tumor growth.

Inherited diseases occur when a person inherits two copies of a defective version of a gene. (A version of a gene is referred to hereinafter as an allele.) Genetic tests can determine which genes and alleles are responsible for a given disease. Once the gene is identified, further testing can identify carriers of the allele and aid researchers in designing treatments for the disease.

Most genetic tests begin by amplifying a portion of the DNA molecule found within a sample of biological material. Amplification is made practical by the polymerase chain reaction (PCR) wherein a DNA synthesizing enzyme (polymerase) is used to make multiple copies of a targeted segment of DNA. By repeating the polymerase copying process, many copies of the targeted segment are produced. For example, thirty (30) repetitions can produce one million (1,000,000) molecules from a single molecule.

Changing the temperature (thermo-cycling) of the test sample drives the PCR reaction. The optimum thermo-cycle varies, however, depending on the material amplified and/or the result sought. In a typical PCR process the sample is heated and cooled to three different target temperatures and is maintained at each temperature for a length of time sufficient for the sample to undergo the desired change. The thermo-cycle begins with heating the sample to about 95° C. to separate the double strands and make them accessible as templates for polymerase replication. Cooling to about 55° C. allows the polymerase initiators (primers) to hybridize with their target DNA segments. Control of the temperature during the hybridization process is critical for accurate hybridization of the primer to the DNA. Heating from 55° C. to about 72° C. is necessary for efficient performance of the polymerase enzyme. At the appropriate temperature, the polymerase reaction catalyzes the elongation of new DNA complementary in nucleotide sequence to the target DNA. At the end of the elongation reaction, heating the solution to about 95° C. causes the newly formed double-stranded DNA to separate into single strands, thus providing templates for another round of PCR amplification.

Current thermo-cycling methods are complex, time consuming and costly. One thermo-cycling device (known as the MJ Research DNA engine) comprises a surface on which are formed micro-wells and under which rests a thermo-electric block for heating and cooling biological material placed in the wells. However, this device takes about one and one-half (1.5) minutes to perform each cycle, even when using a simplified two temperature format. The device thus requires approximately forty-five minutes to perform a thirty cycle run.

Various devices using capillary tubes can perform a thirty cycle run in from ten to thirty minutes. These devices require loading and unloading samples to and from the tubes, sealing the tubes and then exposing the tubes to forced air heating. When the loading and unloading steps are included, these procedures may consume as much as two hours of laboratory time. These procedures also require relatively skilled technicians who can make and load 2-D gels and accurately handle microliter volumes of reagents.

One conventional thermo-cycler uses forced water circulation to heat and cool vessels immersed in a water bath. Three or more reservoirs hold water at different temperatures and rapid pumps and valves bring water from the reservoirs into the bath to produce a huge thermal mass which heats or cools the material in the vessels. Another device used in PCR processes (see European Patent No. 381501) utilizes a flexible bag-like structure with an inner system of chambers. The DNA sample and reagent fluids are loaded into the chambers and the bag is placed on a hot plate for thermo-cycling. After thermo-cycling, the bag is squeezed with external rollers to move the fluid into chambers containing detection reagents.

In all the prior art methods, a significant amount of thermo-cycle time is consumed by ramp periods wherein the temperature of the biological material is changed from one target temperature to the next. The length of each ramp period is a function of both the thermo-cycling equipment and the volume of material heated. The prior art methods generally require first heating the test chamber which then transfers heat to the material contained therein. The thermal mass of the test chamber and volume of material in the test chamber produces high thermal inertia and poor heat-loss surface area to volume ratios. Furthermore, the reagents used in the procedure are expensive and their volume (even if only in the fifty microliter range) can make the procedure prohibitively expensive.

Prior methods pose further time limitations by typically generating only one thermo-cycle at a time. Thus, processing multiple samples at the optimum thermo-cycle of each requires processing the samples one after the other (serial processing). Serial processing may be avoided by using multiple thermo-cyclers, but this approach consumes capital, energy and laboratory space.

Multiple DNA samples can be processed simultaneously using parallel processing. The most common parallel processing technique involves grouping several DNA samples together and subjecting them to a common thermo-cycle. However, the common cycle is necessarily a compromise among the optimum cycles and time savings are thus achieved at the expense of quality of results.

After the material is amplified using one of the foregoing methods it is subjected to further testing. An example of a test which may require PCR amplification as a first step is one which detects the presence of an allele found within a DNA sample. An allele specific oligonucleotide (a substance which will react with the allele and referred to as an ASO hereinafter) is deposited at a known location on a test strip. The DNA sample is labeled using conventional methods, such as by mixing the sample with a fluorescent or radioactive material. The test strip is exposed to the DNA sample. If the sought allele is present it binds with the ASO on the test strip along with the labeling material. The test strip may then be examined to determine if the point where the ASO is deposited exhibits characteristics of the label.

In accordance with the present invention, apparatus is provided which incorporates reaction chambers, heaters and analysis chambers into a miniature self-contained compact structure or cassette. The reaction chambers and heaters are used to simultaneously process extremely small, multiple samples of biological matter at their optimum thermo-cycles. The analysis chambers are used to analyze the results of the reactions. The biological material is maintained within the same cassette for both the PCR and the subsequent analysis, thus many intermediate procedural steps and much of the overall processing time is eliminated or reduced. By using extremely small samples of biological matter and incorporating heaters directly into the cassette structure, thermo-cycling is performed with extremely short ramp periods. The small samples also reduce the overall cost of performing the procedure by minimizing the quantity of expensive reagents required. The cassette is pre-loaded with reagents and analytical materials to further reduce the complexity of the steps which must be performed in the laboratory or clinic, thus making the apparatus amenable for use with automated processes.

The apparatus can be fabricated using flexible circuit technology and methods such as laser machining and photo-lithographic etching. Laser machining of the substrate may be used to provide extremely small reaction and analysis chambers. Photo-lithographic etching may be used to construct heaters which are incorporated into the substrate. Devices using ink jet technology pre-load the device by dispensing extremely small portions of reagents and analytical materials into the reaction and analysis chambers. Various other features and advantages of the invention will become more readily understood from the following description taken in connection with the appended claims and attached drawing in which:

Figure 1:
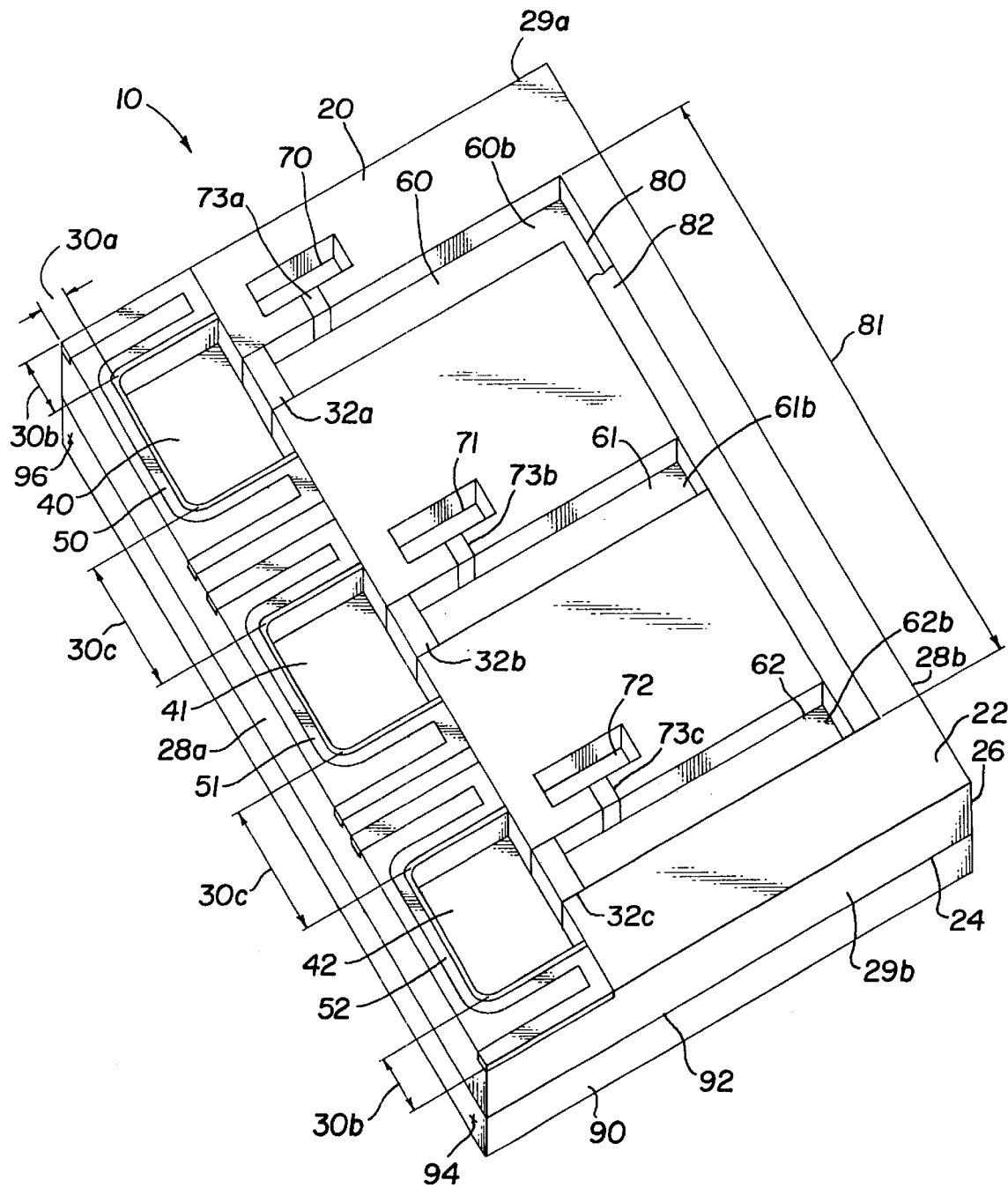
FIG. 1 is a perspective view of a unitary reaction and analysis apparatus constructed in accordance with the invention.

In FIG. 1 the reference character 10 generally refers to compact unitary reaction and analysis apparatus constructed in accordance with the invention. Apparatus 10 comprises a substrate 20 on which are formed or supported reactant valves 32a–32c, reaction chambers 40–42, heaters 50–52, analysis chambers 60–62, solvent reservoirs 70–72, sponge groove 80, collection sponge. 82 and cooler 90. The substrate is preferably formed from alternating layers of materials such as copper and polyimide which are assembled into a unitary body using flexible electronic circuit manufacturing technology. The preferred method of forming the substrate, reaction chambers, heaters and analysis chambers is described in more detail hereinafter in conjunction with the description of FIG. 4. Substrate 20 has a first major face 22 and second major face 24 which define a thickness 26 therebetween. In the presently preferred embodiment, faces 24 and 26 are rectangles of the same size defining long sides 28a and 28b and short sides 29a and 29b therebetween.

Three reaction chambers 40–42 are positioned in the substrate 20 in the embodiment shown in FIG. 1. More or fewer chambers may be provided if desired. Each chamber is spaced a distance 30a from long side 28a and chambers 40 and 42 are spaced a distance 30b from short sides 29a and 29b. The chambers are spaced from each other a distance 30c. The substrate material in spaces 30a–30c maintains the structural integrity of the substrate 20 around the reaction chambers 40–42 and also provides clearances for controllable heaters 50–52 as described hereinafter.

Analysis chambers 60–62 are positioned in substrate 20 with each analysis chamber in fluid communication with one of reaction chambers 40–42. The number, arrangement and interconnection of the analysis chambers may be varied or changed as desired but each reaction chamber will typically be connected to at least one analysis chamber. Reactant valves 32a–32c are positioned to control flow of fluids from the reaction chambers into the analysis chambers.

Solvent reservoirs 70–72 are positioned adjacent analysis chambers 60–62, respectively, and solvent valves 73a–73c are positioned to control flow of solvents from the solvent reservoirs into the analysis chambers. Alternative embodiments (not shown) may include more, fewer or no solvent reservoirs or may alter the arrangement and interconnections between solvent reservoirs and analysis chambers. If the apparatus does not include a solvent reservoir, solvent may be supplied from an external reservoir or reservoirs as described in more detail hereafter.

A sponge groove 80 of length 81 is formed in the first major face 22 and extends from analysis chamber 60 to analysis chamber 62. A collection sponge 82 positioned in groove 81 extends from chamber 60 to chamber 62 and is in fluid communication with each analysis chamber. Alternative embodiments (not shown) may employ separate sponges in fluid communication with one or more chambers or may not use a sponge.

A heat sink 90 is secured to the second major face 24 with thermally conductive adhesive 92 or the like. The heat sink may be a conventional thermo-electric device or the like and/or may have a finned surface or the like. In the case of thermo-electric coolers, terminals 94 and 96 provide interconnections for external circuitry, controls, etc. Heat sink 90 may comprise a plurality of independently controllable thermo-electric coolers with each cooler in thermal contact with a reaction chamber.

Reaction chamber 40 (shown in greater detail in FIG. 2) is illustrative of chambers 40–42. Chamber 40 is defined by a floor 43 positioned within the thickness 26 of the substrate 20, walls 44a–44e (formed by the body of the substrate), wall 44f (formed by valve 32a) and an open top 46 positioned at the first major face 22. Walls 44a–44f form a substantially rectangular chamber in the illustration of FIG. 2. In the preferred embodiment the chamber has a length and a width of at least fifty microns. However, the chamber may assume any geometry amenable to containing fluids undergoing the desired reaction. Similarly, the floor 43 is flat in the illustration of FIG. 2 but may be concave, convex or any other geometry desired. The term "floor" as used herein thus refers to any surface or surfaces forming all or part of the reaction chamber which is positioned within the thickness of the substrate.

Figure 2:
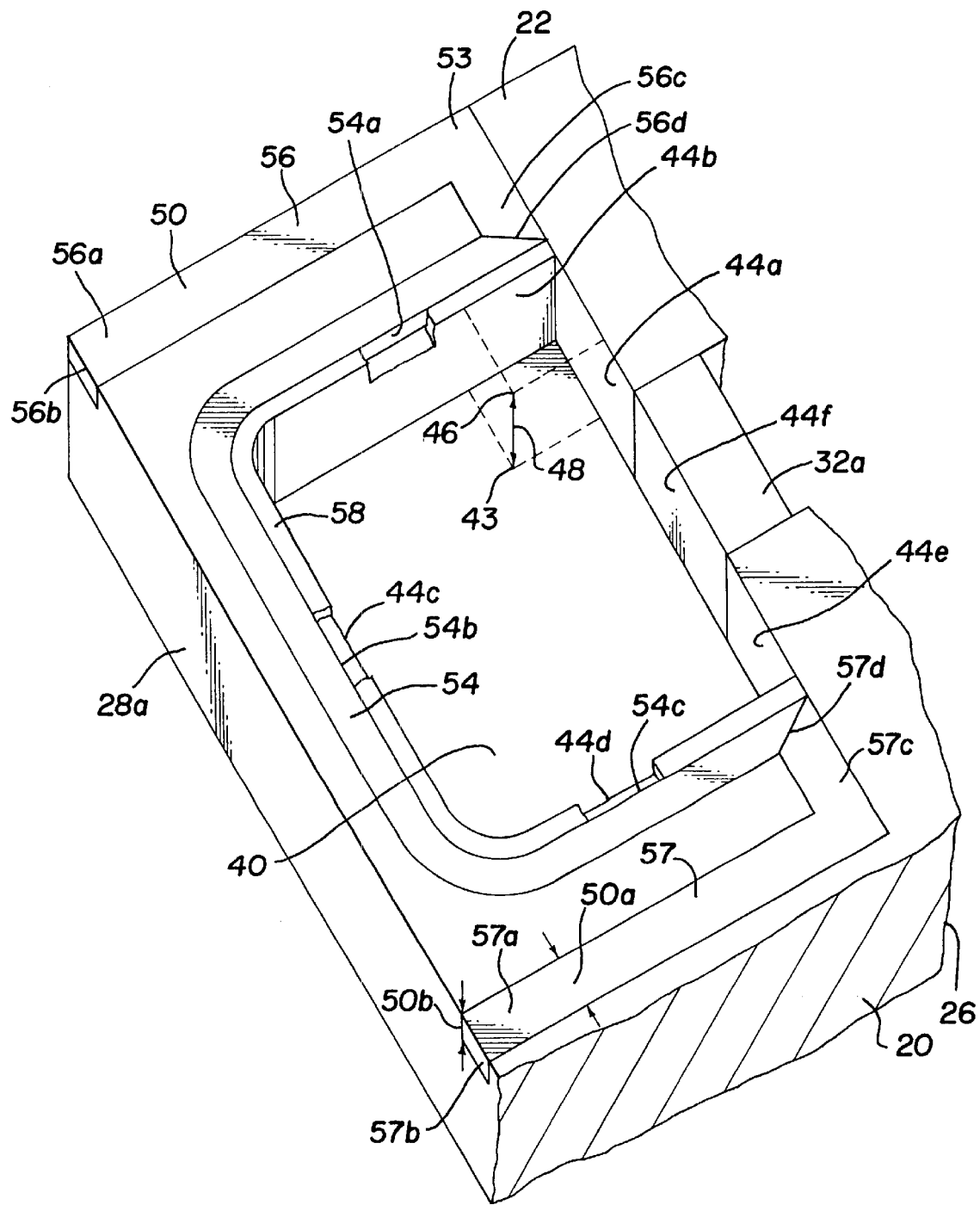
FIG. 2 is an enlarged perspective view of the reaction chamber shown in the apparatus of FIG. 1.

Reaction chamber 40 is adapted to hold liquids up to a depth 48 equal to the vertical distance between the open top 46 and the floor 43 as illustrated in FIG. 2. The floor 43 may be positioned at any depth within the thickness 26 of the substrate. Each reaction chamber 41–42 may thus have a different depth as well as the other geometrical features hereinbefore described.

Controllable resistance heater 50 (shown in greater detail in FIG. 2 and illustrative of heaters 50–52) is integrally formed within the substrate. For purposes of this disclosure, any heater having a heating element in thermal contact with a reaction chamber is suitable. In FIG. 2 heater 50 is shown embedded in substrate 20 with the top surface 53 of the heater flush with the first major face 22. The heater may also be positioned on top of the first major face 22 or within the body of the substrate 20.

Heater 50 has a U-shaped resistance heating element 54 and L-shaped terminals 56 and 57. Terminals 56 and 57 have first end portions 56a and 57a, respectively, which extend to and lie flush with long side 28a. The exposed end portions form interconnect pads 56b and 57b which are connectable to an external power source (not shown). The interconnect pads may protrude from or recede into side 28a and may be positioned at or near any other surface of the substrate. The interconnect pads may also include any conventional means for interfacing with external circuitry. Each pair of interconnect pads may be simultaneously connected to independently controlled power sources, thus permitting each heater to be controlled independently of the others.

Terminals 56 and 57 have second end portions 56c and 57c which are joined to heating element 54 at joints 56d and 57d to form a continuous piece therewith having a width 50a and a substantially constant thickness 50b. The width 50a may vary over the length of the heater and is sized to permit the heating element 54 and terminals 56 and 57 to lie within spaces 30a–30c (shown in FIG. 1) with heating element 54 in thermal contact with reaction chamber walls 44b–44d. The heater may be formed from any of a variety of electrically resistive materials such as nickel/chromium alloys, suitably doped semiconductors, etc.

The heating element 54 has interior walls 54a–54c positioned to follow the contour defined by reaction chamber walls 44b–44d. The resistive heater element 54 is electrically isolated from the reaction chamber walls by a spacer section 58. Spacer section 58 electrically insulates the heating element 54 from the contents of the reaction chamber 40 but is thin enough to permit rapid and efficient heat transfer from the heating element 54 to any material contained in the reaction chamber.

Figure 3:
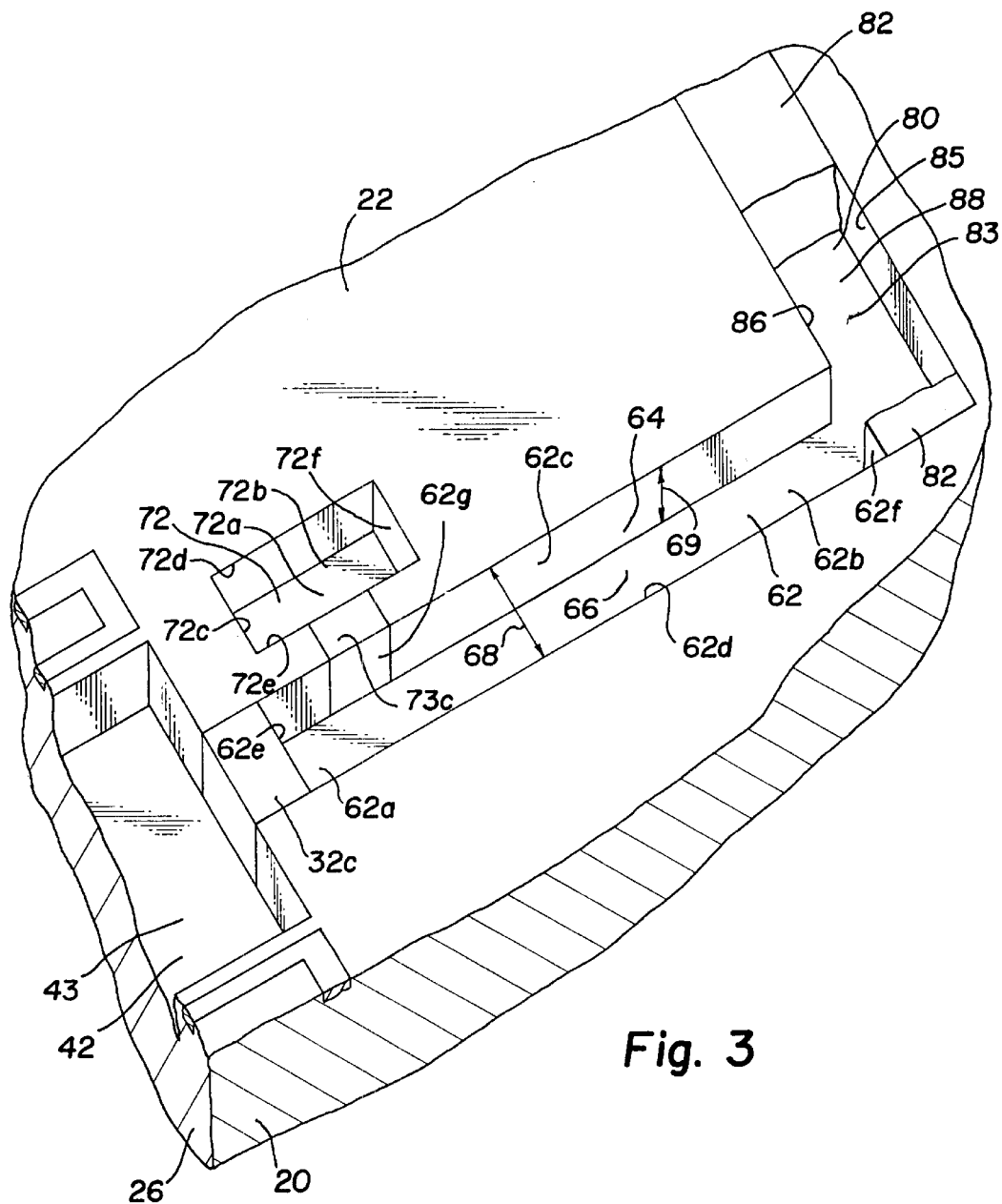
FIG. 3 is an enlarged perspective view of the analysis channel shown in the apparatus of FIG. 1.

Analysis chamber 62 (shown in greater detail in FIG. 3 as illustrative of analysis chambers 60–62) is a channel having a first end 62a in fluid communication with reaction chamber 42 via valve 32c. Second end 62b is in fluid communication with the collection chamber 80. Reactant valve 32c is positioned in the first end 62a to control the flow of fluid from the reaction chamber into the analysis channel. Collection sponge 82 is positioned in the collection chamber 80 to absorb fluids from the analysis chamber. Each analysis chamber has a window 64 positioned at the first major face 22 and a lower surface 66 positioned within the thickness 26 of the substrate 20. The term "window" as used herein refers to any unobstructed opening (as shown in FIG. 3) and to transparent covers (not shown). The term "transparent" as used herein refers to materials through which photometric and/or other types of analysis can be performed. If a cover is used it will be applied after diagnostic probes (described in detail hereafter) or other analytical materials are deposited in the chamber and will include a vent or air hole if necessary to allow fluid to flow within the chamber. In addition to a lower surface and a window, each analysis chamber has walls 62c and 62d formed by the substrate and walls 62e–62g formed by portions of the reactant valve 32c, collection sponge 82 and solvent valve 73c.

The space between walls 62c and 62d defines a channel width 68. In the preferred embodiment the channel width is sized to provide a capillary for drawing fluids from reaction chamber 42 and may be as small as ten (10) micrometers in diameter. In the preferred embodiment, the channel is 100 to 500 μm wide. Other embodiments (not shown) may include gravity feed provisions or micro-pumps to move fluid from the reaction chambers to the analysis chambers. The vertical distance between the window 64 and the lower surface 66 as viewed in FIG. 3 defines a channel depth 69.

The lower surface 66 may be positioned at any point within the thickness 26 of substrate 20 to provide analysis chambers of different depths. Each analysis chamber 60–62 may have a different depth and the other geometrical features may vary from chamber to chamber as hereinbefore described. In the preferred embodiment, the lower surface 66 in each analysis chamber is positioned within the thickness 26 of substrate 20 to coincide with the corresponding reaction chamber floor 43.

As illustrated in FIG. 1 sponge groove 80 is formed in the first major face 22 and extends across and connects the second ends 60b, 61b and 62b of analysis chambers 60–62. As best shown in FIG. 3, the groove 80 has a bottom 83 positioned within the thickness 26 of substrate 20. The bottom preferably coincides with or extends below the lower surface 66 of each analysis chamber. Each groove 80 has side walls 85 and 86 which define an opening 88 in the first major face 22.

A collection sponge 82 having exterior dimensions substantially corresponding to the dimensions of the sponge groove is positioned in groove 80. Any suitable conventional sponge material may be used and secured by conventional means such as adhesive or the like. If desired the sponge may be made with dimensions slightly larger than the groove to provide an interference fit with the walls of the groove.

Solvent reservoir 72 (illustrative of solvent reservoirs 70–72 as shown in greater detail in FIG. 3) is defined by a lower surface 72a positioned within the thickness 26 of the substrate 20, an opening 72b positioned at the first major face 22, and side walls 72c–72f. The reservoir is in fluid communication with analysis chamber 62 near first end 62a so that solvent from the reservoir will traverse most or all the length of channel 62 before the solvent is absorbed by the sponge 82. Solvent valve 73c controls the flow of solvent from the reservoir into the analysis chamber.

Each reservoir holds enough solvent to clean one channel. Reservoirs of different volumes can be provided to meet various other requirements. For example, in an alternative embodiment (not shown) a single solvent reservoir is placed in fluid communication with more than one channel and the volume of the single reservoir is increased to hold enough solvent to clean all the channels. In other embodiments (not shown) the solvent reservoir may be connected to or form a part of the reaction chamber or analysis chamber.

The term "valve" as used herein refers to any type of seal or barrier which may be operated or ruptured to permit fluid to flow from the reaction chamber or solvent reservoir into the analysis chamber. For example, a valve can comprise a pressure or heat sensitive membrane which is ruptured after the PCR reaction occurs in the reaction chamber. Reactant valve 32c (and 32a–32b) and solvent valve 73c (and 73a–73b) may be any suitable gate means for controlling flow and may be operated by mechanical, electrical, magnetic or chemical means. The valves used may vary, of course, depending on local size limitations, chemicals processed, operating conditions such as heat and pressure, etc.

Figure 4:
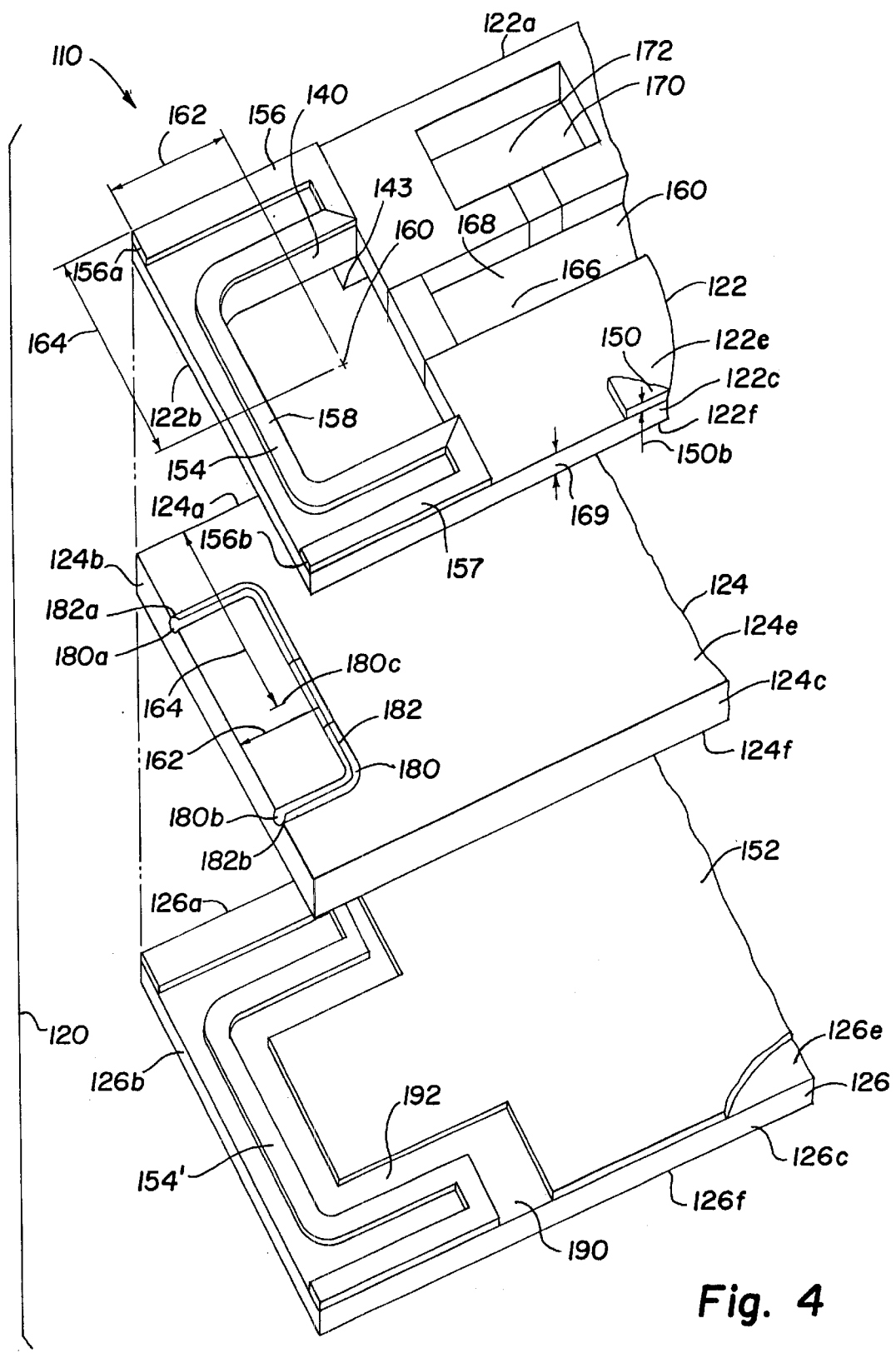
FIG. 4 is an exploded view of an alternative embodiment of the invention.

Apparatus embodying the principles of the invention is shown in exploded view in FIG. 4 to illustrate one method of making same. Although apparatus 110 of FIG. 4 shows only one reaction chamber, analysis chamber, etc., it is to be understood that the apparatus may include a plurality of such components. The apparatus 110 of FIG. 4 comprises a substrate 120 preferably having at least one metallic and at least one non-metallic layer secured together by conventional flex circuit manufacturing techniques. As used herein a "metallic layer" means a layer comprised of electrically conductive material (which may be a metal, an alloy, a metal solution, etc.) and a "non-metallic layer" means a layer comprised of substantially electrically non-conductive material. The number, shape, arrangement and sequencing of the various layers may vary considerably. Thus FIG. 4 merely illustrates one substrate embodiment which can be constructed using flex circuit manufacturing techniques.

Substrate 120 includes upper, middle and lower non-metallic layers 122, 124 and 126, respectively. While a number of non-metallic materials may be used to form the layers, polyimide is preferred. The substrate also includes metallic layers 150 and 152.

Upper layer 122 is formed by cutting a sheet of polyimide to define sides 122a–122c, a first major face 122e and a bottom surface 122f. A similarly sized sheet of metal or foil 150 having a thickness 150b equal to the desired thickness of heater 154 is secured to the first major face 122e. While virtually any metallic layer may be used, a highly conductive metal such as copper, aluminum or gold is preferred.

Portions of the sheet metal 150 are removed from the upper polyimide layer 122 by any suitable process such as photo-lithographic etching or the like. A portion 154 of the sheet metal which is not removed remains secured to the first major face 122e of the polyimide layer to define a heater. Various other methods may be used to form the heater. For example, heater 154 could be stamped from sheet metal and then secured to first major face 122e by conventional means.

In the preferred embodiment heater 154 is formed of copper terminals 156 and 157 and a nickel/chromium alloy heating element 158. The copper terminals 156 and 157 are formed and secured to first major face 122e as hereinabove described. A nickel/chromium heating element 158 may be similarly formed and secured or it may be formed on the major face 122e by methods such as vapor deposition, sputtering, etc. The heater also includes interconnect pads 156a and 156b which extend to side 122b for connection to an external power source.

After the required portions of sheet metal are removed, chambers and channels are formed in first major face 122e of upper polyimide layer 122. In the preferred embodiment, portions of the polyimide are removed in a controlled process such as ablation by an excimer laser or the like. The reaction chamber 140 is formed with its center 160 located a distance 162 from side 122b and a distance 164 from side 122a. An analysis chamber 160, a solvent reservoir 170 and a sponge groove (not shown) are similarly formed. By using excimer lasers, the chambers and grooves may be formed with geometric features as small as ten (10) micrometers or less. The chambers and grooves in any of the possible embodiments will typically be formed with at least some geometric features in the range of 10 to 1,000 $\mu$m. The term "geometric features" refers to a chamber or channel's depth, width, length, diameter, etc., but excludes features such as corner radii and chamfers.

The first major face 122e is shown ablated to a depth 168 which positions reaction chamber floor 143 and lower surfaces 166 and 172 within the thickness 169 of the upper polyimide layer 122. However, the ablation process can be used to position the floor and lower surfaces anywhere within the total thickness of the assembled substrate 120. For example, floor 143 can be positioned within the thickness of substrate layer 124 if desired.

The process may be varied to produce various embodiments of the substrate 120. For example, the major face 122e may be ablated to provide clearances for the heater 154 such that the heater lies flush with the first major face 122e (see FIG. 1).

The middle layer 124 is formed by cutting a sheet of polyimide to define sides 124a–124c, upper surface 124e and bottom surface 124f. A portion of the upper surface 124e is removed to form a groove 180 for a temperature measuring device. Preferably, the groove is sized to accommodate a thermocouple wire having a diameter of, for example, twenty-five micrometers (25 $\mu$m). The thermocouple groove has ends 180a and 180b which extend to and open at side 124b. However, the groove may be oriented with ends 180a and 180b positioned at any of the other sides or surfaces, if desired.

The groove center 180c is positioned a distance 162 from side 124b and a distance 164 from side 124a. Thus, when the layers of the substrate are assembled a thermocouple wire 182 installed in the groove 180 will be positioned in thermal contact with the center 160 of the reaction chamber floor 143 positioned in upper polyimide layer 122. The thermocouple wire 182 has ends 182a and 182b which terminate at or about side 124b and may connected to external circuitry by conventional means.

Alternatives to using a thermocouple wire include using thin film thermocouples. Thin film thermocouples may comprise a separate layer (not shown) within the substrate 120, thus eliminating the need to form a thermocouple groove. Thin film thermocouples may also be incorporated into portions of a polyimide layer.

The lower polyimide layer 126 is formed by cutting a sheet of polyimide to define sides 126a–126c, an upper surface 126e and a second major face 126f. A lower metallic layer 152 is secured to the upper surface 126e and portions of the metallic layer (for example, areas 190 and 192) are removed to form heater 154'. Heater 154' is shown with the same geometry as heater 154. However, heater 154' may assume any geometry which places it in thermal contact with the reaction chamber. Heater 154' may also be formed by alternative methods as hereinbefore described. A plurality of heaters (for example 154 and 154') may thus be provided within the substrate 120 adjacent the reaction chamber 140. Furthermore, by providing multiple layers (for forming heaters) and spacing them appropriately, the heaters may be positioned adjacent the reaction chamber at the levels necessary for rapidly and uniformly heating materials contained in the reaction chamber. Thus, it is to be understood that the term "heater" as used herein can include one or more single layer heaters positioned adjacent the same reaction chamber.

Figure 5:
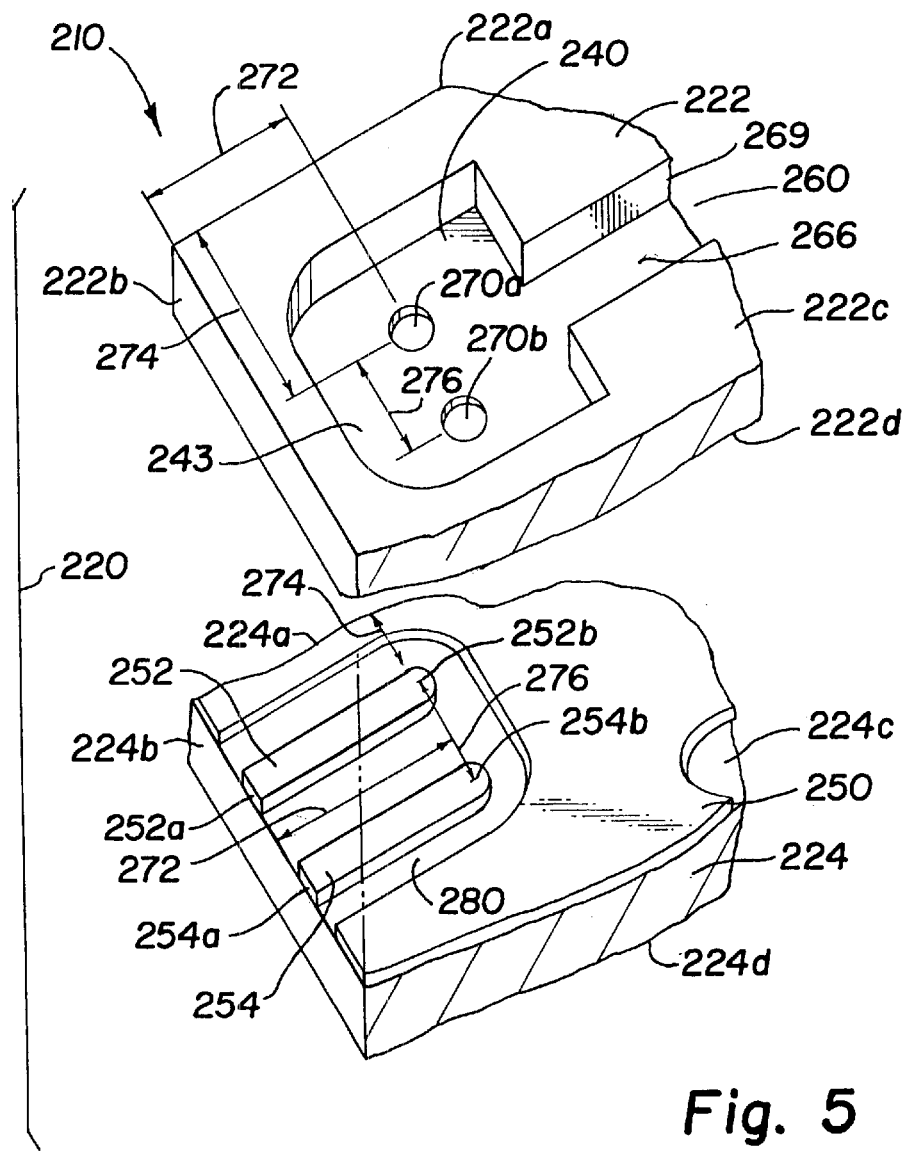
FIG. 5 is a fragmentary exploded view of the apparatus of FIG. 1 illustrating the formation of an ohmic heater therein.

FIG. 5 illustrates a portion of an alternative embodiment 210 which employs an ohmic heater. For purposes of this disclosure, an ohmic heater is one which employs the material being heated as an electrical resister and thus generates heat by passing current through the material to be heated.

Substrate 220 includes upper polyimide layer 222, lower polyimide layer 224 and metallic layer 250. Upper polyimide layer 222 is formed by cutting a sheet of polyimide to form at least sides 222a–222b, a first major face 222c and a bottom surface 222d. The first major face 222c is ablated with an excimer laser or the like to remove material and form reaction chamber 240 and analysis chamber 260 as hereinbefore described. Material is removed to position floor 243 and lower surface 266 at a depth 269 with the polyimide layer.

The floor 243 of reaction chamber 240 is further ablated to provide two holes 270a and 270b which extend entirely through the layer 222 and bottom surface 222d. Each hole is spaced from side 222b a distance 272. Hole 270a is spaced a distance 274 from side 222a and hole 270b is spaced a distance 276 from hole 270a.

Lower polyimide layer 224 is similarly formed with at least sides 224a–224b, an upper surface 224c and a lower major face 224d. Metal layer 250 is secured to the upper surface 224c and portions 280 are removed to form a heater comprising positive terminal strip 252 and negative terminal strip 254. (The stated polarity is for illustrative purposes only and may be reversed if desired.) The strips may also carry alternating current.

The strips have interconnect pads 252a and 254a positioned at side 224b for connecting to an external power source. The interconnect pads can be positioned at any side or surface and may include conventional means for connecting to external circuitry. The strips also have fluid interface pads 252b and 254b. Both fluid pads are positioned a distance 272 from side 224b. Pad 252b is positioned a distance 274 from side 224a and pad 254b is positioned a distance 276 from pad 252a. Thus, when the layers of the substrate are assembled together, the fluid interface pad 252b is positioned directly beneath hole 270a and fluid interface pad 254b is positioned beneath hole 270b. A current path is provided between the fluid interface pads when the reaction chamber 240 is filled with fluid and the fluid is heated by the electrical resistance of the fluid as current is transmitted therethrough. The terminal strips are preferably formed of copper. Fluid pads 252b and 254b are preferably plated with a corrosion-resistant material such as platinum.

Figure 6:
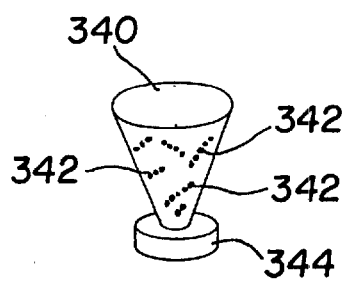
FIG. 6 is a schematic of an electro-magnetic induction heater.

FIG. 6 illustrates an electro-magnetic induction heater. A reaction chamber 340 of any suitable geometry has a quantity of magnetic beads 342 deposited in the chamber walls. Additionally or alternatively, fluids placed in the chamber may have magnetic beads dispersed therein. A magnetic field created by the solenoid 344 causes the beads to vibrate and generate heat, thus warming material in the chamber 340. The solenoids 344 may be secured to the substrate or external to the substrate. The term "heater" as used in connection with this embodiment includes the magnetic beads alone and magnetic beads in conjunction with a solenoid secured to the substrate.

Figure 7:
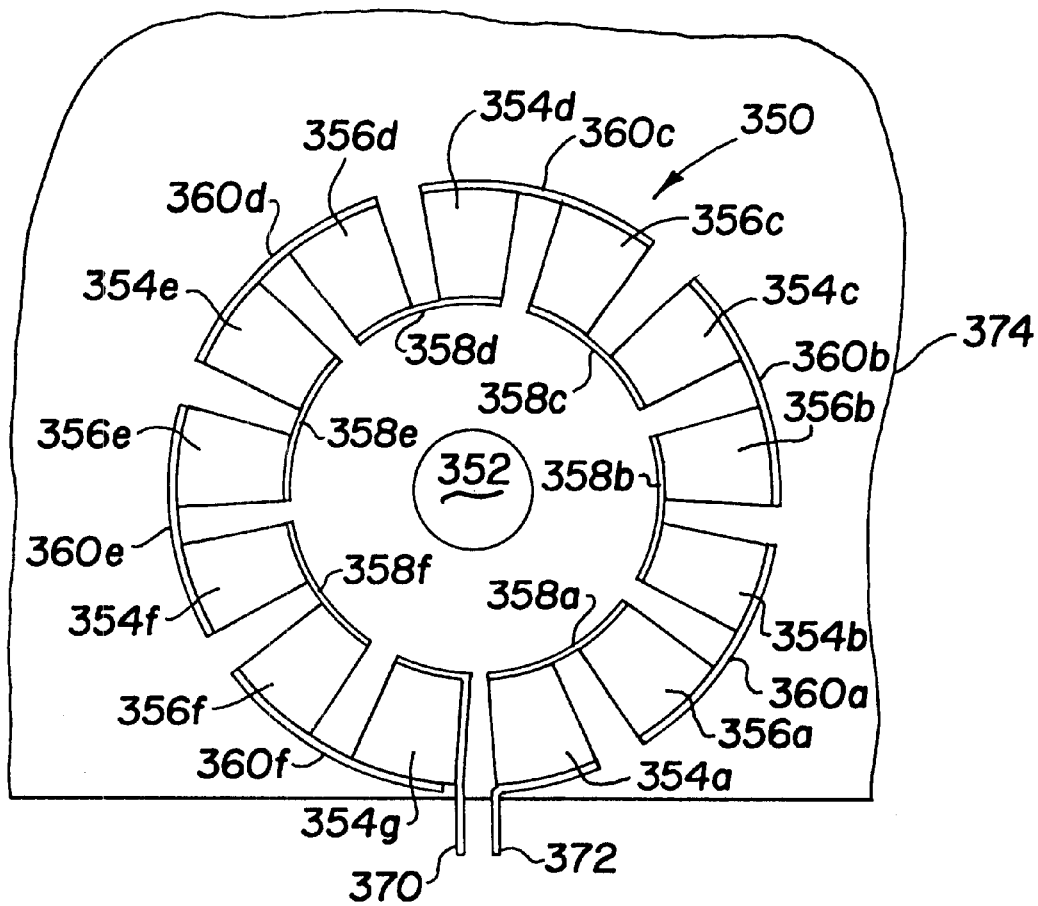
FIG. 7 is a diagrammatic representation of a thermo-electric thermo-cycling apparatus constructed in accordance with the invention.

FIG. 7 illustrates an embodiment having a thermo-electric heater incorporated directly into the substrate. The thermo-electric device may be constructed from N-type and P-type semiconductor materials or from dissimilar metallic materials. The blocks can be formed by conventional methods such as photo-lithographic etching, laser machining, etc.

The N-type and P-type blocks are formed into a circular row 350 around reaction chamber 352. The row comprises N-type blocks 354a–354g and P-type blocks 356a–f which are arranged in sequentially alternating order. Each block is electrically connected to the adjacent blocks by internal traces 358a–358f and external traces 360a–360f. The traces are preferably metallic material such as copper and are formed by a process such as photo-lithographic etching. The row of blocks pumps heat radially inward toward the reaction chamber 352 when current of the appropriate polarity is applied to terminals 370 and 372. The row 350 depicted in FIG. 7 is shown positioned within the substrate 374 below the analysis channel (not shown). Multiple rows may also be provided at different levels within the body of the substrate.

Figure 8:
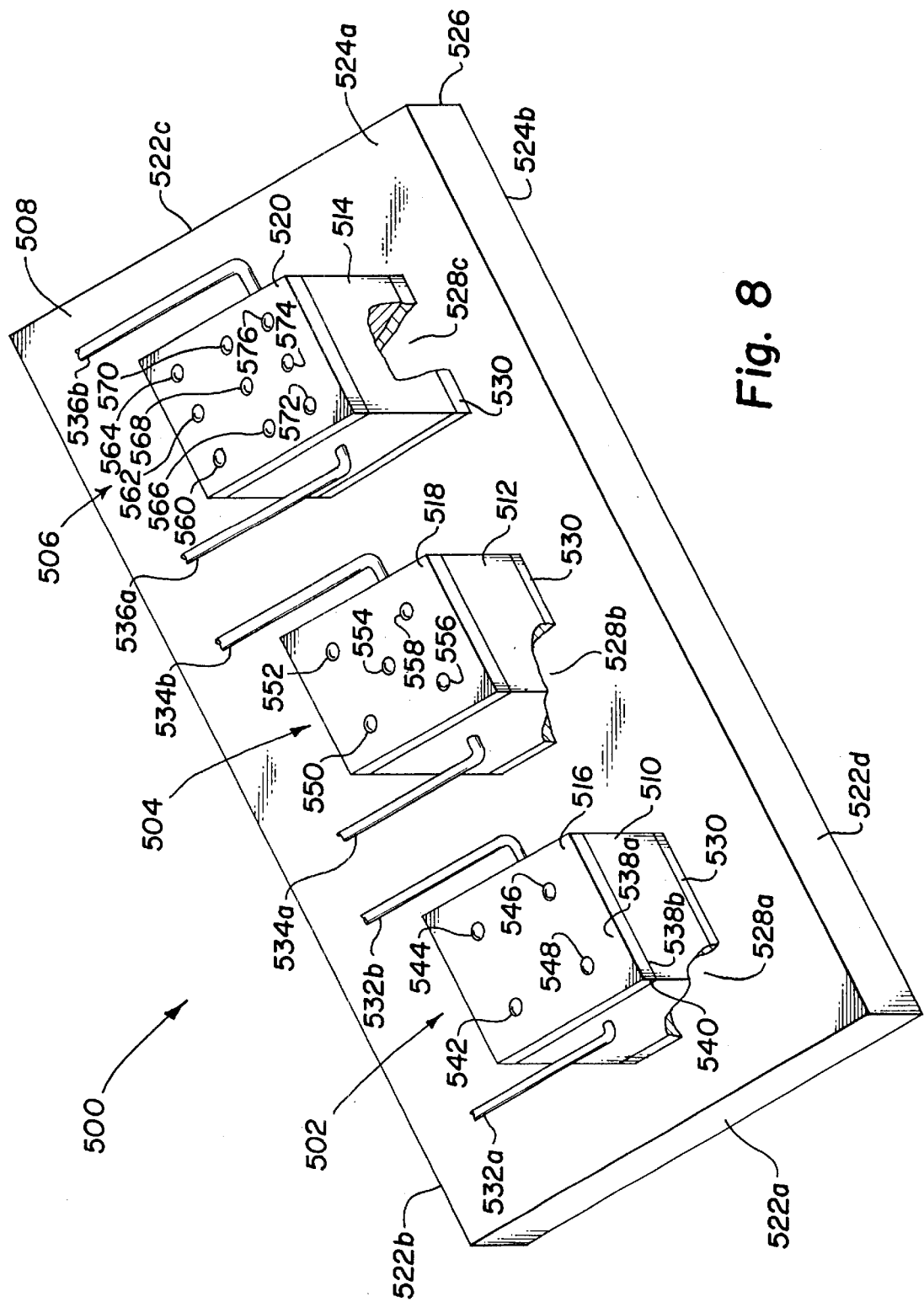
FIG. 8 is a perspective view of a multi-substrate thermo-cycling device.

FIG. 8 illustrates an embodiment of the invention which uses a thermo-electric device. The embodiment is generally indicated by reference numeral 500 and includes three temperature cycling units 502, 504 and 506 mounted on platform 508. The temperature cycling units comprise thermo-electric units (referred to hereinafter as modules) 510, 512, 514 and substrates 516, 518, 520, respectively.

The platform 508 is preferably a rectangular sheet having sides 522a–522d. An upper surface 524a is offset from lower surface 524b by a thickness 526. Platform 508 may function as a heat sink for the temperature cycling units and is thus preferably made from material (such as aluminum) which is both rigid and thermally conductive.

The upper surface 524a will typically encompass an area large enough to support from one (1) to two hundred fifty-six (256) temperature cycling units, but the area can be increased to accommodate greater numbers of units if desired. The units are secured to contact areas 528a, 528b and 528c, respectively, using thermally conductive adhesives 530 or other conventional means. The contact areas can be abraded, knurled or otherwise treated to increase the adhesive gripping area.

The modules 510–512 are preferably constructed from N-type and P-type semiconductor materials but may also be constructed from dissimilar metallic materials. The N-type and P-type semiconductor materials are formed into blocks, and each module typically comprises at least one row (hereafter referred to as a stage) of alternating N-type and P-type blocks. Stages can be stacked vertically (cascaded) so that heat is pumped from one stage to the next to increase the heating/cooling capacity of the module. The stages may have different numbers or sizes of blocks; the blocks in various stages may be made from different materials; and/or each stage may operate at different current levels.

The modules have terminal leads 532a–532b, 534a–534b and 536a–536b connected to external controls (not shown) which power the modules. The external controls operate each of the modules independently of the others and can be any conventional arrangement of programmable controllers, power supplies, switches, etc. The controls also include a means for reversing the polarity of the current supplied to each module. Accordingly, the modules may pump heat either into or away from the substrates 516, 518 and 520, depending on the polarity of the current at the leads.

Substrate 516 is illustrative of substrates 518 and 520 and comprises an electrically non-conductive, thermally conductive material such as polyimide. The substrate has oppositely disposed major faces 538a and 538b with a thickness 540 therebetween. Portions of the substrate are removed to form reaction chambers 542, 544, 546 and 548 by any suitable means such as laser machining, etc., and each reaction chamber has an open top and a floor positioned within the thickness of the substrate as hereinbefore described. In the preferred embodiment the substrate is about 0.25 inch by about 0.25 inch so that two hundred fifty-six (256) independently controllable temperature cycling units can be placed on a platform 508 about four inches by four inches.

The substrates can be fabricated with analysis chambers, solvent reservoirs, sponges, etc., as hereinbefore described. A separate heater integrally formed with the substrate as hereinbefore described is thus not needed in this embodiment.

After the substrate is formed the reaction chambers and analysis channels are loaded with the reagents and analytical material needed to perform and analyze a bio-chemical reaction. Preferably, the chambers and channels are loaded by depositing drops of fluid on the reaction chamber floors and analysis channel lower surfaces. The material in the reaction chambers will generally remain in a fluid state while the drops deposited in the analysis channels will adhere to the lower surfaces and thus remain anchored in place during subsequent handling and positioning of the analysis apparatus. The anchored drops can be discrete or overlapping and may be positioned randomly or arranged in a pattern.

Figure 9:
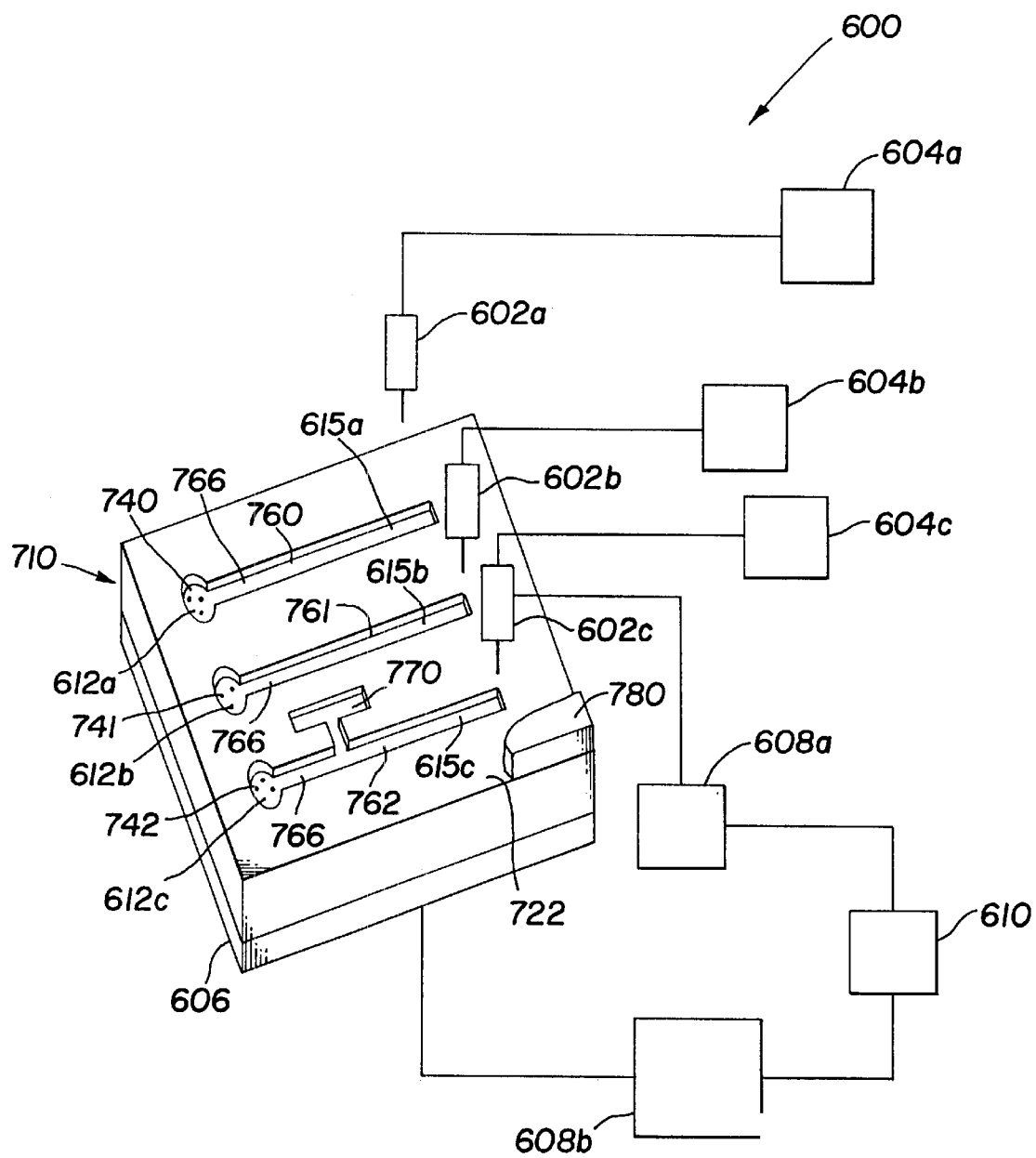
FIG. 9 is a schematic representation of dispensing apparatus for pre-loading analysis chambers in apparatus formed in accordance with the invention.

A dispenser for depositing drops of fluid into the reaction chambers and analysis channels is illustrated in FIG. 9 and designated generally by the numeral 600. An analysis apparatus 710 is shown in conjunction with the dispensing apparatus. The dispensing apparatus comprises a plurality of fluid dispensers 602a–602c, a plurality of reservoirs 604a–604c, and an X-Y positioning table 606. The fluid dispensers and X-Y table are connected to drive electronics 608a and 608b, both of which are controlled by programmable controller 610. A complete description of suitable dispensing apparatus and methods for using same is disclosed in application for United States Letters Patent entitled Methods and Apparatus for Making Miniaturized Diagnostic Arrays filed concurrently herewith under Ser. No. 08/524, 781, now U.S. Pat. No. 5,658,802 disclosure of which is incorporated herein by reference.

Reservoirs 604a–604c are connected to dispensers 602a–602c and filled with reagents necessary to perform a bio-chemical reaction. For example, in the case of PCR reactions the reservoirs may be filled with reagents comprising fluorescently-tagged primers, nucleotides, buffer salts, etc.

Programmable controller 610 and drive electronics 608b operate the X-Y table 606 to position the reaction chambers 740–742 beneath the dispensers 602a–602b. Programmable controller 610 and drive electronics 608a activate the dispensers to eject drops of reagents 612a–612c into the reaction chambers 740–742. The size of fluid drops dispensed may vary depending on the size and geometry of the reaction chamber. Thus, when the reaction chambers are extremely small (50 µm by 50 µm, for example) the dispensing apparatus may dispense correspondingly small drops of fluid, for example, in the range of 10 pl to 1 nl. After the desired quantity of reagent is dispensed, the X-Y table 606 repositions reaction chambers 740–742 beneath different dispensers (not shown) which deposit different reagents in the reaction chambers. This process is repeated until each reaction chamber contains the desired number and quantity of reagents.

The X-Y table next positions the analysis channels 760–762 beneath the fluid dispensers. The various components in the dispensing apparatus 600 are operated as hereinbefore described to deposit quantities of fluids which form probes 615a–615c on the lower surfaces 766 of the analysis chambers 760–762. When the bio-chemical reaction performed in the reaction chamber is amplification of an allele with PCR, for example, the fluids may be allele specific oligonucleotides (ASOs) which react with the amplified allele.

The probes may be formed from pre-synthesized materials. Alternatively, the probes can be synthesized in place on the lower surface by depositing the appropriate fluids one on top of the other. One or more probes may be deposited in each analysis channel. The pattern of deposited probes may vary depending upon, for example, the number of probes, the size of the probes and the analysis chamber or channel geometry. The probes may be deposited to form linear arrays, for example, in each analysis channel or square arrays, for example, in a square-shaped analysis chamber. The dispensing apparatus hereinbefore referenced can form discrete probes with center-to-center spacings as small as twenty five micrometers (25 µm), if desired. The preferred spacing of the probes is a center to center distance of about 25 to about 1000 µm.

In embodiments which include a solvent reservoir 770, it may be desireable to load solvent into the reservoirs at the same time the reagents and probes are loaded into the reaction chambers and analysis channels. The same dispensing apparatus hereinbefore described may be used to deposit the solvent into the reservoirs.

The solvent will typically remain in a liquid state and may have a tendency to vaporize. The reagents deposited in the reaction chamber will typically remain fluid. A cover 780 can be secured to the first major face 722 to seal the solvent and reagents into the reservoirs and reaction chambers. The cover 780 is preferably made of two parts. One part seals the reaction chamber and is removable so that test samples may be later added. The second part seals the solvent reservoir and may be permanently secured to first major face 722. If the second part of cover 780 also covers the analysis channels, it is preferably made of transparent material so that it does not interfere with photometric or other analysis later performed on materials in the channels. In embodiments where the solvent is not pre-loaded into the reservoir, cover 780 may comprise a single removable portion which covers only the reaction chambers.

Figure 10:
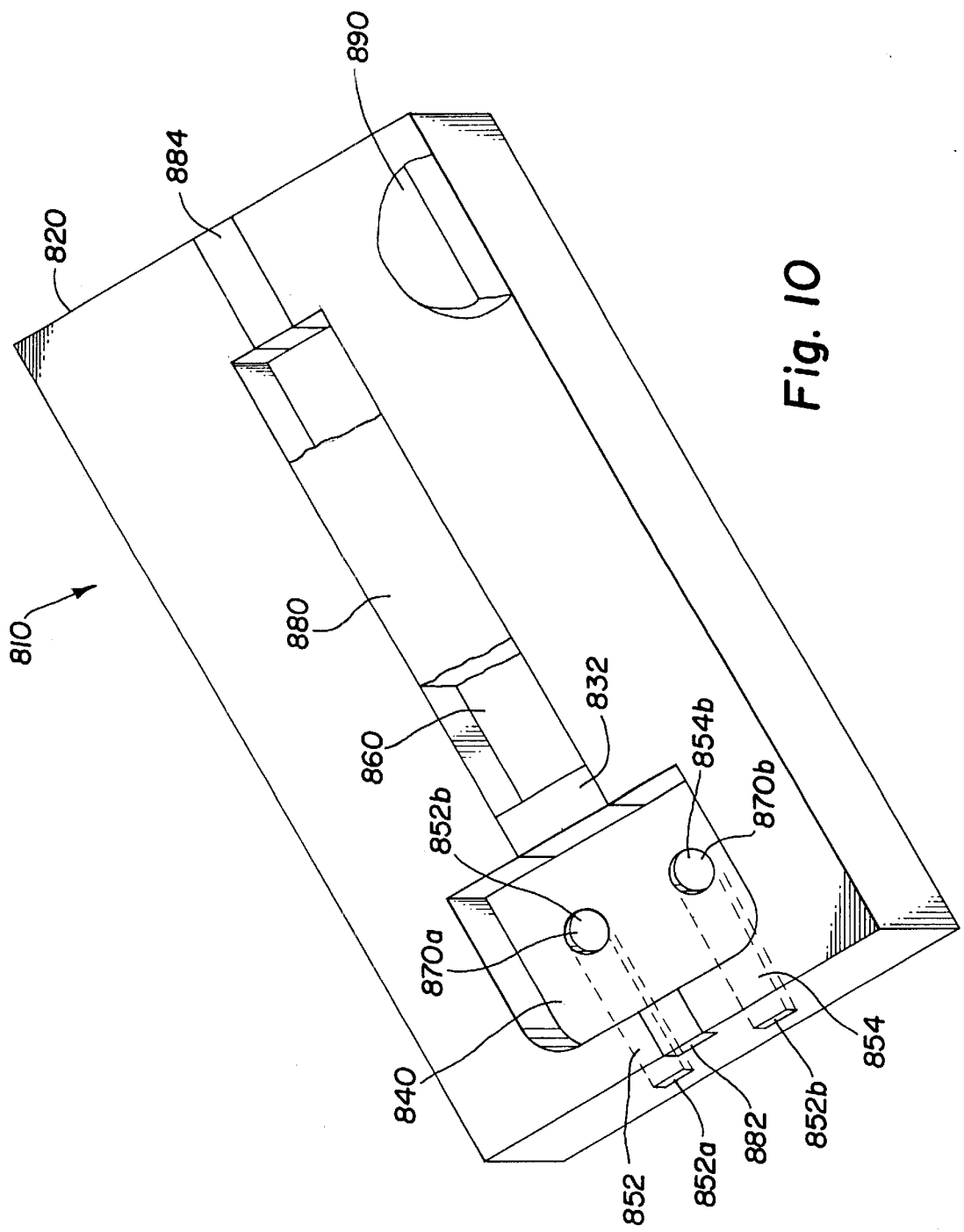
FIG. 10 is a perspective view of an embodiment of the invention using electrophoretic gel.

An alternative embodiment 810 in which the results of bio-chemical reaction can be analyzed using electrophoresis is illustrated in FIG. 10. Embodiment 810 comprises a substrate 820 constructed as hereinbefore described using an excimer laser or the like to ablate the substrate 820 and form reaction chamber 840, analysis chamber 860 and holes 870a and 870b. A heater having terminals 852 and 854 with interconnect pads 852a and 854a and fluid interface pads 852b, 854b is formed integrally with the substrate. However, any of the heater or heater/cooler embodiments hereinbefore described may be used. The reaction chamber 840 is loaded with reagents used in a bio-chemical reaction and a reactant valve 832 positioned as shown to control fluid flow between reaction chamber 840 and analysis channel 860. Analysis channel 860 is filled with analytical material comprising an electrophoretic gel 880 (for example, a 1% agarose gel) and a suitable material (for example, ethidium bromide) can be used to stain the nucleic acids in the gel for monitoring the fluorescence of the amplified product. Electrodes 882 and 884 are provided at opposite ends of the analysis channel 860. Electrode 884 is in direct electrical contact with the electrophoretic gel. Electrode 882 makes electrical contact with the gel when the reaction chamber 840 is filled with liquid or, alternatively, electrode 882 may be positioned in direct contact with the gel. A transparent cover 890 placed over the analysis channels retains the gel in the channel.

Figure 11:
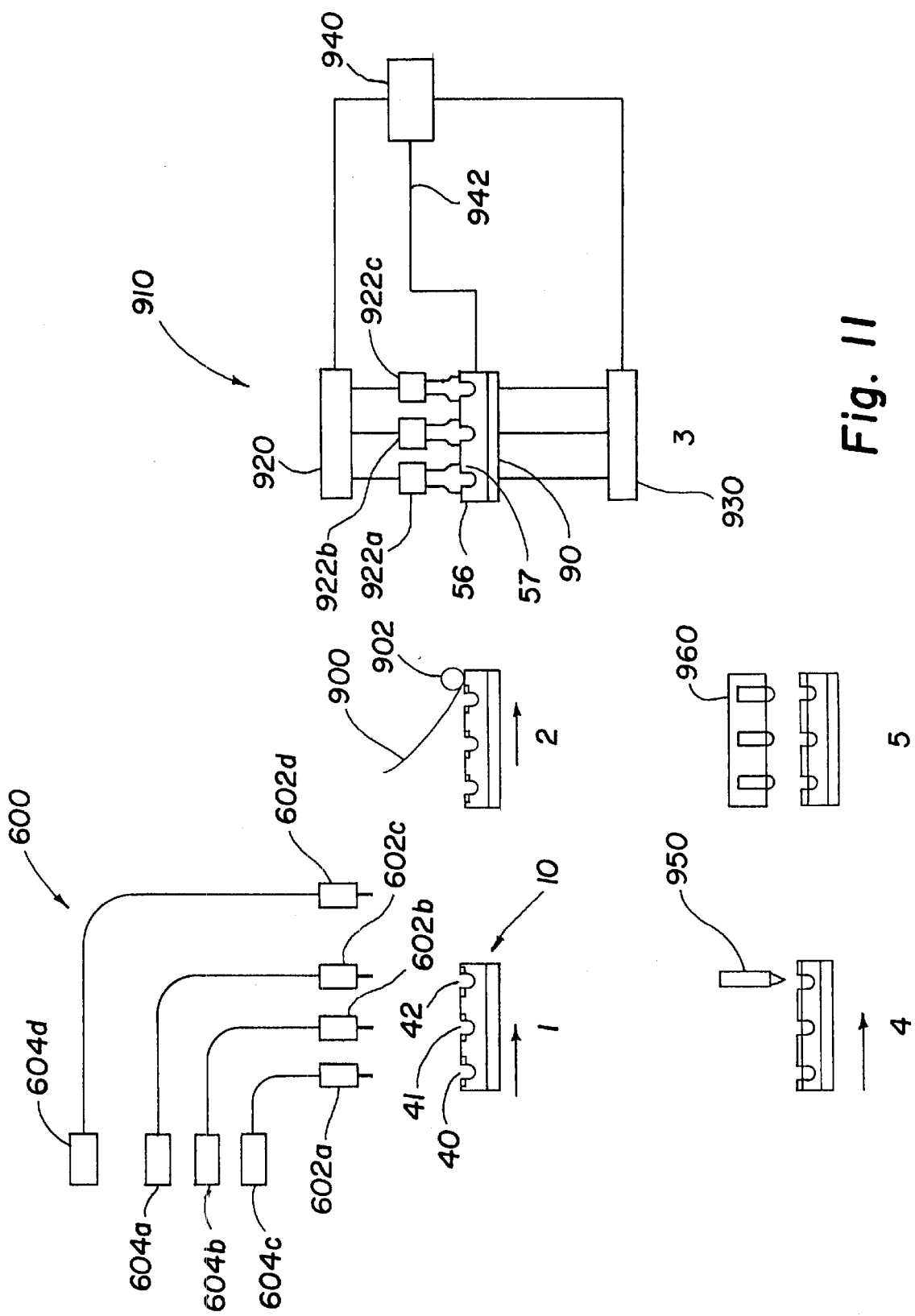
FIG. 11 is a flow diagram of a method for performing an analysis in accordance with the invention.

A method of using the analysis apparatus of FIG. 1 is represented schematically in FIG. 11. The method may be adapted to use any of the embodiments hereinbefore discussed. The portion of cover 780 (FIG. 8) sealing the reagents into the reaction chambers is removed and, at position 1, a fluid dispensing system 600 similar to that used to dispense reagents and probes is used to load the reaction chambers 40–42. Each reservoir 604a–604c is filled with a material which undergoes a bio-chemical reaction with the reagents previously placed in the reaction chambers. The reservoirs may each be loaded with the same sample material, if desired, or they may be loaded with different sample materials. For example, each reservoir may contain a DNA sample from the same or from different cancer patients. The reaction chambers 40–42 are positioned beneath the dispensers 602a–602c and drops of fluid containing the DNA material are dispensed into the reaction chambers. If the analysis apparatus has not been pre-loaded with solvent, then a fourth dispenser 602d and reservoir 604d may be provided to deposit solvent into the solvent reservoirs.

Fluids containing the DNA material and the solvents will typically remain fluid and have a tendency to vaporize during the thermo-cycle. To prevent loss of these materials, the apparatus is treated as shown at position 2 where a cover 900 is secured to the first major face 22 by roller 902. The size of the cover 900 and the portions of the major face 22 to which it is applied may vary. For example, if solvents are pre-loaded and sealed in place with covers 780 (see FIG. 9), then covers 900 need only seal the reaction chambers. If the cover 900 overlaps any portion of the analysis channels, then the cover 900 is preferably transparent.

After the cover 900 is applied, the analysis apparatus 10 is positioned at a thermo-cycling control station 910 as shown at position 3. The thermo-cycling control station comprises a heater control 920, a cooler control 930 and programmable controller 940. The heater control 920 may be a conventional commercial temperature controller or the like. A variable transformer may be used to vary the power distributed to the heaters.

The thermocouples (not shown) are connected to the programmable controller 940 with connections 942 and the controller 940 is connected to the heater and cooler controls 920 and 930. The heater control 920 includes heater connections 922a–922c which are adapted to interface with terminals 56 and 57. The cooler control 930 is connected to cooler 90. The cooler control may be an air blower which circulates air over a finned heat sink, for example, or an electrical power source when cooler 90 comprises one or more thermo-electric coolers or other electrical devices.

Programmable controller 940 signals heater control 920 to send current through the heater terminals 56 and 57 to heat the materials in the reaction chambers to the first target temperature. The temperature in each of the reaction chambers is monitored by thermocouples which relay the information to the programmable controller 940. After the first target temperature is reached, controller 910 and 940 reduces the current to maintain the temperature level for the required time period. When the specified time period has elapsed, the current is reduced so that cooler 90 can rapidly draw the material temperature down to the next target temperature in the thermo-cycle.

The thermo-cycle continues through the various target temperatures and time periods until the PCR reaction is complete. Since each heater is controlled independently of the others to provide various thermo-cycles, multiple samples of DNA can be processed simultaneously at the optimum thermo-cycle of each. Furthermore, by using small quantities of fluids and heaters and coolers as hereinbefore described, changing from one target temperature to another may occur almost instantaneously.

In the embodiment using the ohmic heating (FIG. 5), the heater control preferably comprises a high power audio amplifier used in conjunction with a standard function generator. Frequencies in the kilohertz range are preferable.

In the embodiment using electro-magnetic induction (FIG. 6), the power and control unit from an electromagnetic precision soldering iron is placed beneath each of the reaction chambers if it is not secured to the substrate. Activation of the power unit creates a magnetic field sufficient to vibrate the beads in the reaction chamber, thus warming the fluids therein.

In the embodiment using a thermoelectric heater (FIG. 7) current of the appropriate polarity is applied to the terminals to pump heat into the chamber. The level of the current is adjusted up or down to pump the amount of heat necessary to achieve and maintain the target temperatures.

After the thermo-cycle is complete, the analysis apparatus is moved to position 4 where the reactant valves (not shown) are operated to allow the amplified PCR material to flow into the analysis chambers. Operation of the valves or seals may be by mechanical, chemical, electrical or magnetic means, etc., depending on the type of valve or seal used. For example, if a pressure sensitive seal is used, a stylus 950 can be positioned over the seal and lowered with sufficient force to rupture the seal. The stylus 950 may also be used to puncture covers 780 and/or 900 to provide vent holes necessary for allowing any fluid materials in the apparatus to flow.

The analysis apparatus may be positioned to gravity feed the fluid into the channels. In the preferred embodiment, however, fluid is drawn into the channels by capillary action. The fluid passes over the probes deposited on the analysis channel floors and is absorbed into the sponge. The solvent valves or seals are similarly operated to allow the solvent to wash through the analysis channels and clean residual fluids which have not reacted with a probe. In embodiments which do not include solvent reservoirs, the solvent may be applied at this time directly into the reaction chamber or analysis channel by external means such as the fluid dispensers hereinbefore described, extremely fine capillaries, etc. If necessary, stylus 950 or other means can be used to puncture a hole in cover 780 and/or 900 to provide solvent access to the internal portions of the apparatus.

After the solvent cleans the analysis channels, the analysis apparatus is moved to position 5 where a photometric or other analyzer 960 or the like is used to locate the probes which have reacted with the amplified material.

To use an embodiment employing electrophoretic analyses, the foregoing steps are performed generally as described above except that it may not be necessary to clean the analysis channel with solvents. After the reactant valves are operated to place the fluid in the reaction chamber in communication with the analysis channel, an electric current is applied to the fluid and the gel in the channel through terminals 882 and 884.

Figure 12:
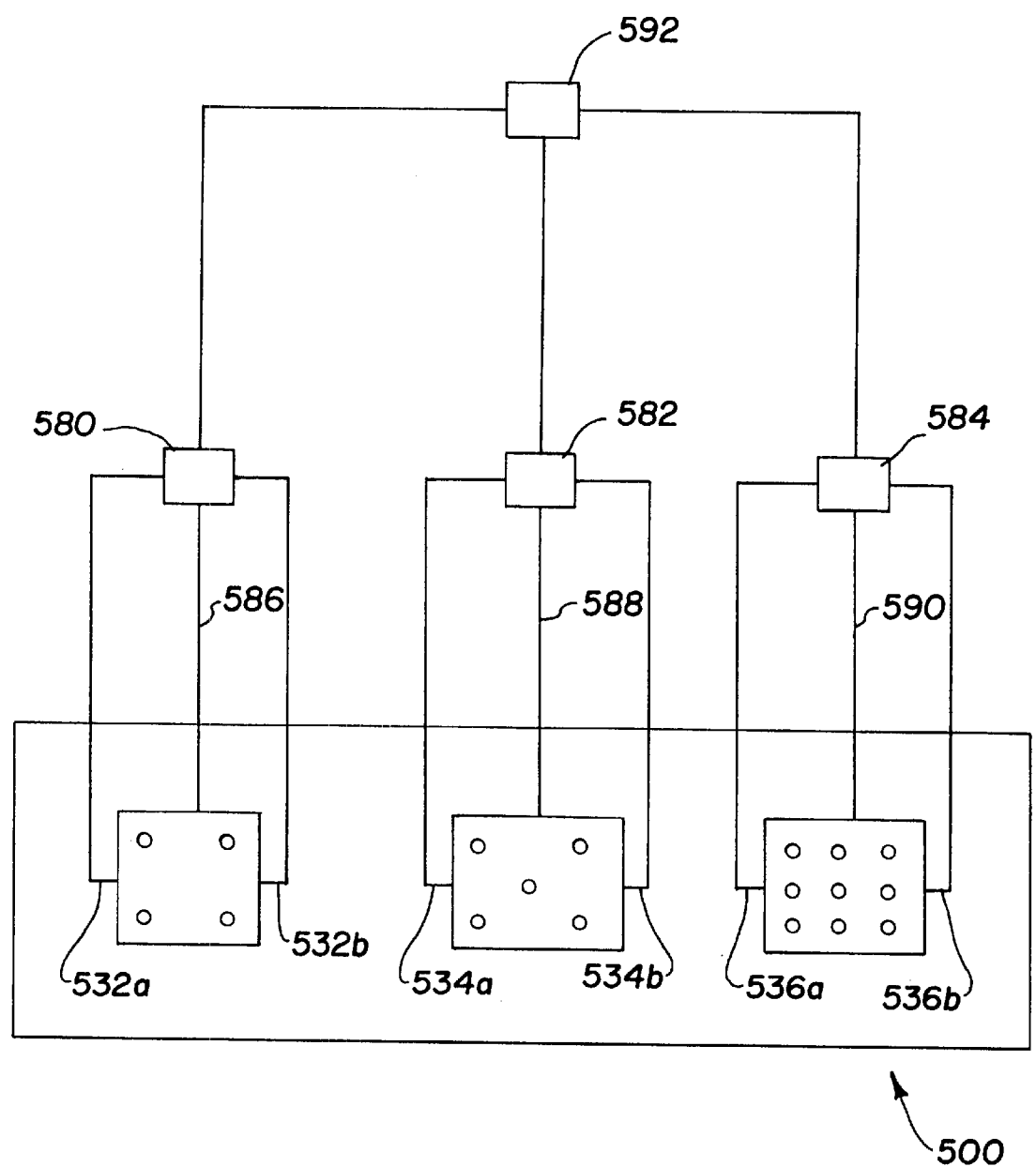
FIG. 12 is a diagrammatic representation of a method of using the apparatus of FIG. 8.

A method for using the apparatus illustrated in FIG. 8 is shown schematically in FIG. 12. Leads 532a–532b, 534a–534b and 536a–536b are connected to power sources 580, 582 and 584, respectively. Thermocouples (not shown) are also connected to the power sources via connections 586, 588 and 590, respectively. The power sources are connected to programmable controller 592.

Suitable power sources and programmable controllers are well known in the art as is the manner of connecting them. The power sources include means for reversing the polarity of the current supplied to the temperature cycling units.

After the biological material is placed in the reaction chambers and the chambers are covered as hereinbefore described, the controller 592 begins the thermo-cycle by signalling the power sources 580, 582 and 584 to send current to the thermo-electric modules. The thermocouples monitor the temperatures of the materials in the chambers and signal the power sources when the various target temperatures are reached. Since each module is controlled independently of the others, the number of thermo-cycles which may be performed simultaneously is limited only by the number of thermo-electric modules.

In a typical thermo-cycle involving target temperatures of 95° C., 55° C. and 72° C., the thermocouple signals the power source when the first temperature of 95° C. is reached. After the material in the reaction chambers has been maintained at 95° C. for the desired time period, the power source reduces the current supplied to the thermo-electric module to lower the material temperature to the next target temperature of 55° C. Alternatively, since 55° C. is above standard room temperature, the power source may shut off current flow and allow the heat sink effect of the environment to draw down the temperature of the material. As a further alternative, the power source can supply current of a reversed polarity to the modules so that they pump heat away from the reaction chambers.

After the material temperature reaches 55° C the power source must maintain, increase or reverse the polarity of the current (depending on the method used to lower the temperature) to maintain the material at 55° C. for the desired time period. The current is then increased to raise the material temperature to 72° C. The foregoing steps are repeated until the desired thermo-cycle is completed.

From the foregoing it will be recognized that the principles of the invention may be employed in various arrangements to obtain the benefits of the many advantages and features disclosed. In particular, methods of using various embodiments have been described with reference to various steps and commercially available apparatus. Preferably, commercial apparatus will combine into one machine each of the foregoing steps in an automated process. It is to be understood, therefore, that although numerous characteristics and advantages of the invention have been described, together with details of the structure and function of various embodiments of the invention, this disclosure is illustrative only. Various changes and modifications may be resorted to, especially in matters of detail such as shape, size and arrangement of parts, without departing from the spirit and scope of the invention as defined by the appended claims.

What is claimed is:

1. Apparatus having microfabricated chambers for conducting biochemical analysis, comprising:
    a flexible substrate of the kind used in flexible circuit manufacturing technology comprising an ablatable polymeric material having a first major face and a bottom surface;
    a plurality of ablated miniature reaction chambers spaced apart in the first major face, said chambers being produced by ablation;
    a metallic layer fixed to the substrate and associated with each of the plurality of reaction chambers, the metallic layer comprising a plurality of independently controllable heaters configured to raise the temperature of the reaction chamber which a given heater is associated with;
    a plurality of ablated analysis chambers spaced apart in the first major face of the substrate, each being in fluid communication with a reaction chamber, said analysis chambers being produced in the substrate by ablation;
    each reaction chamber and analysis chamber having a lower surface in the substrate; and
    a protective cover layer positioned over the reaction chambers.

2. Apparatus as defined in claim 1 including a solvent reservoir formed in said substrate and in fluid communication with said analysis chamber.

3. Apparatus as defined in claim 1 including reagent material useful in performing a PCR process, deposited in said reaction chamber.

4. Apparatus as defined in claim 1 wherein said analysis chamber is a channel having a first end in fluid communication with said reaction chamber and an oppositely disposed second end.

5. Apparatus as defined in claim 4 including a collection sponge in fluid communication with said second end.

6. Apparatus as defined in 1 including an analytical material useful in performing a PCR process positioned in said analysis chamber.

7. Apparatus as defined in claim 6 wherein said analytical material comprises discrete probes anchored to said lower surface.

8. Apparatus as defined in claim 6 wherein said analytical material is an electrophoretic gel.

9. Apparatus as defined in claim 1 including a temperature measuring device positioned in thermal communication with said reaction chamber.

10. Apparatus as defined in claim 1 including a heat sink in thermal communication with said reaction chamber.

11. Apparatus as defined in claim 10 wherein said heat sink comprises a cooler which is controllable to maintain a desired temperature.

12. Apparatus as defined in claim 1 including a plurality of reaction chambers and a plurality of controllable heaters with each heater positioned in thermal communication with at least one reaction chamber and controllable independently of the other heaters.

13. Apparatus as defined in claim 1 including a valve controlling fluid flow between said reaction chamber and said analysis chamber.

14. Apparatus having microfabricated chambers for conducting biochemical analysis; comprising
    a flexible substrate comprising an ablatable polymeric material having a first major face and a second major face defining a thickness therebetween;
    a plurality of ablated reaction chambers spaced apart in the first major face, said chambers having an open top and a floor positioned within said thickness;

a plurality of individually controllable heaters integrally formed within said substrate, each heater positioned in thermal communication with at least one of said reaction chambers;

a plurality of ablated analyses chambers, each positioned in a path of fluid communication with at least one of the reaction chambers and having a window at one of the major faces and a lower surface positioned within said thickness; and a plurality of valves controlling flow of fluid between each reaction chamber and a corresponding analysis chamber.

15. Apparatus as defined in claim 14 including at least one ablated solvent reservoir in fluid communication with at least one of said analysis chambers.

16. Apparatus as defined in claim 14 including at least one temperature measuring device positioned in thermal communication with at least one of said reaction chambers.

17. Apparatus as defined in claim 16 wherein said temperature measuring device is a thermocouple.

18. Apparatus as defined in claim 16 wherein said temperature measuring device is a thin film thermocouple.

19. Apparatus as defined in claim 14 including at least one controllable cooler positioned in thermal communication with at least one of said reaction chambers.

20. Apparatus as defined in claim 14 wherein said substrate comprises at least one metallic layer and at least one non-metallic layer.

21. Apparatus as defined in claim 20 wherein at least one of said heaters comprises at least a portion of said metallic layer.

22. Apparatus as defined in claim 14 wherein at least one of said heaters is a resistance heater.

23. Apparatus as defined in claim 14 wherein at least one of said heaters is an ohmic heater.

24. Apparatus as defined in claim 14 wherein at least one of said heaters includes magnetic beads positioned in said substrate adjacent a reaction chamber.

25. Apparatus as defined in claim 14 wherein at least one of said heaters comprises a thermoelectric device positioned to encircle said reaction chamber and pump heat into the chamber.

26. Apparatus as defined in claim 14 wherein at least one of said analysis chambers comprises a channel having a first end and a second end with said first end in fluid communication said reaction chamber.

27. Apparatus as defined in claim 26 wherein said channel is sized to draw fluids from said reaction chamber through capillary action.

28. Apparatus as defined in claim 27 wherein said second end is in fluid communication with a sponge.

29. Apparatus as defined in claim 14 wherein at least one of said valves is pressure operated.

30. Apparatus as defined in claim 14 wherein at least one of said valves is chemically operated.

31. Apparatus as defined in claim 14 wherein at least one said valves is electrically operated.

32. Apparatus as defined in claim 14 wherein said analysis chambers and said reaction chambers have at least some opposite walls within the chambers spaced apart within the range of 10 to 1000 micrometers.

33. Apparatus having microfabricated chambers for conducting biochemical analysis, comprising:

a plurality of flexible substrates of the kind used in flexible circuit manufacturing technology comprising an ablatable polymeric material, each substrate having first and second oppositely disposed major faces defining a thickness therebetween;

at least one ablated reaction chamber formed within each substrate, having an open top at one of said major faces and a floor positioned within said thickness wherein said at least one reaction chamber is produced by ablation;

a thermo-electric module positioned in thermal communication with each said substrate; and an ablated analysis chamber in a path of fluid communication with each said reaction chamber, said analysis chamber having a window at one of said major faces and a lower surface positioned within said thickness.

34. Apparatus as defined in claim 33 including a solvent reservoir formed in at least one said substrate and in fluid communication with said analysis chamber.

35. Apparatus as defined in claim 33 including reagent material useful in performing a PCR process, deposited in said reaction chamber.

36. Apparatus as defined in claim 33 wherein at least one said analysis chamber is a channel having a first end in fluid communication with said reaction chamber and an oppositely disposed second end.

37. Apparatus as defined in claim 36 including a collection sponge in fluid communication with said second end.

38. Apparatus as defined in 33 including an analytical material useful in performing a PCR process, positioned in said analysis chamber.

39. Apparatus as defined in claim 38 wherein said analytical material comprises discrete probes anchored to said lower surface.

40. Apparatus as defined in claim 38 wherein said analytical material is an electrophoretic gel.

41. Apparatus as defined in claim 33 wherein at least one substrate includes a temperature measuring device.

42. Apparatus as defined in claim 33 wherein at least one substrate includes a valve controlling fluid flow between said reaction chamber and said analysis chamber.

43. Apparatus as defined in claim 33 including individual controls for controlling the polarity and flow of current through each said thermo-electric module.

44. Apparatus having microfabricated chamber for conducting biochemical analysis, comprising:

a plurality of flexible substrates of the kind used in flexible circuit manufacturing technology comprising an ablatable polymeric material, each substrate having first and second oppositely disposed major faces defining a thickness therebetween;

at least one ablated reaction chamber formed within each substrate, having an open top at one of said major faces and a floor positioned within said thickness wherein said at least one reaction chamber is produced by ablation;

a thermo-electric module positioned in thermal communication with each said substrate; and individual controls for controlling the polarity and flow of current through each said thermo-electric module.

45. Apparatus as defined in claim 44 wherein at least one said substrate includes an analysis chamber in fluid communication with said reaction chamber having a window at one of said major faces and a lower surface positioned within said thickness.

46. Apparatus as defined in claim 45 wherein said chamber is a channel sized to draw fluids from said reaction chamber through capillary action.

47. Apparatus as defined in claim 45 including a solvent reservoir formed in at least one said substrate and in fluid communication with said analysis chamber.

48. Apparatus as defined in claim 44 wherein at least one substrate includes a temperature measuring device.

49. Apparatus as defined in claim 44 wherein at least one substrate includes a valve controlling fluid flow between said reaction chamber and said analysis chamber.

50. Apparatus as defined in claim 49 wherein said valve is pressure operated.

51. Apparatus as defined in claim 49 wherein at least one of said valves is chemically operated.

52. Apparatus as defined in claim 49 wherein at least one of said valves is electrically operated.

53. Apparatus as defined in claim 44 further comprising an analysis chamber in fluid communication with each said reaction chamber having a window at one of said major faces and a lower surface positioned within said thickness.

* * * * *